United States Patent [19]

Endo et al.

[11] Patent Number: 5,043,283

[45] Date of Patent: Aug. 27, 1991

[54] FLUIDIZED BED CELL CULTURE APPARATUS WITH A DRAIN VALVE FOR THE REMOVAL OF SUPPORT MATERIAL

[75] Inventors: Isao Endo, Kokubunji; Teruyuki Nagamune, Kamifukuoka; Tetsuo Kobayashi, Kobe, all of Japan

[73] Assignees: Rikagaku Kenkyusho; Shinko-Pfaudler Company Ltd., both of Japan

[21] Appl. No.: 124,826

[22] Filed: Nov. 24, 1987

[30] Foreign Application Priority Data

Nov. 26, 1986 [JP] Japan ................... 61-281192

[51] Int. Cl.$^5$ ........................... C12M 3/02
[52] U.S. Cl. ..................... 435/286; 435/284; 435/289; 435/311; 435/313; 422/103; 422/140; 210/150
[58] Field of Search ................. 435/284–286, 435/291, 311, 313, 316, 803, 813, 818, 288, 299, 310; 422/140, 144, 145, 146, 147, 103; 210/661, 670, 616, 612, 618, 150, 151; 261/62, 94, 95; 137/544, 547, 550

[56] References Cited

U.S. PATENT DOCUMENTS

| | | | |
|---|---|---|---|
| 2,146,326 | 2/1939 | Bergius et al. | 435/313 |
| 3,013,950 | 9/1959 | Gavin | 435/284 |
| 3,754,993 | 8/1973 | Oguchi et al. | 210/661 |
| 3,829,478 | 8/1974 | Ohorodnik et al. | 422/140 |
| 4,218,538 | 8/1980 | Church | 435/313 |
| 4,337,315 | 6/1985 | Fukushima | 435/313 |
| 4,545,909 | 10/1985 | Atkinson et al. | 435/285 |
| 4,649,117 | 3/1987 | Familletti | 435/313 |
| 4,675,113 | 6/1987 | Graves et al. | 210/635 |

FOREIGN PATENT DOCUMENTS 0197299 10/1986 European Pat. Off. .

OTHER PUBLICATIONS

Rehm et al. Eds., Biotechnology, vol. 2, "Fundamentals of Biochemical Engineering", (Deerfield Beach, Fla., VCH, 1985) pp. 447–509.
Oda, Continuous Alcohol Fermentation Technologies Using Immobilized Yeast Cells, pp. 597–610.
Rehm, Biotechology, vol. 2, 1985; Chapter 20–21, pp. 445–517.
Manual of Industrial Microbiology and Biotechnology, Editors Arnold L. Demain and Nadine A. Solomon; pp. 66–83 (1986).
Chemical Abstracts, vol. 83, 1975, p. 376.
"A Continuous, Farm-Scale, Solid-Phase Fermentation Process for Fuel Ethanol and Protein Feed Production from Fodder Beets", by William R. Gibbons, Carl A. Westby and Thomas L. Dobbs, pp. 1098–1107, Biotech./Bioengineering, vol. 26, No. 9, (1984).
"Tissue Culture Methods and Applications", edited by Paul F. Kruse, Jr., and M. K. Patterson, Jr.; pp. 372–376, (1973).

*Primary Examiner*—David L. Lacey
*Assistant Examiner*—William H. Beisner
*Attorney, Agent, or Firm*—Brumbaugh, Graves, Donohue & Raymond

[57] ABSTRACT

Cell culture apparatus comprises a fluidized bed culture tank body in which cell attached porous material is fluidized by air flow, and a pre-culture tank for supplying medium to the fluidized bed culture tank body according to the amount of the liquid medium which is taken out of the fluidized bed culture tank body. By the use of a drain valve which can be controlled to remove liquid medium and porous material or just liquid medium, the cell culture apparatus can continuously produce metabolite.

10 Claims, 6 Drawing Sheets

FLUIDIZED BED CELL CULTURE APPARATUS WITH A DRAIN VALVE FOR THE REMOVAL OF SUPPORT MATERIAL

FIELD OF THE INVENTION

This invention relates to cell culture apparatus in which microorganisms, particularly fungi such as molds, actinomycetes, animal cells, plant cells or so on are attached to carriers of porous material which are fluidized in liquid medium by air flow and grow to continually produce useful substances such as antibiotics, enzymes, proteins, polysaccharides, physiological active substances, and animal and plant hormones.

DESCRIPTION OF THE PRIOR ART

It is well known that submerged culture methods have been used in culture of molds or actinomycetes, and primary metabolite such as glycerin or alcohol and secondary metabolite such as penicillin or streptomycin have been produced in industrial scale by means of an air flow agitation tank and so on.

Persons including some of this inventors proposed a novel cell culture method and apparatus in unexamined Japanese Patent Publication No. 60(1985)-21487 and Japanese Utility Model Application No. 60-23142, respectively. In the cell culture method, cells to be proliferated are attached to porous material suspended in liquid medium and cell culture is carried out in much higher efficiency than the prior arts since cells grow in porous material instead of liquid medium. In the cell culture apparatus, cell growth and separation of cells and liquid medium including metabolite can be carried out with one apparatus. The above proposed method and apparatus attract attention in the field because production efficiency of metabolites such as penicillin is extremely high.

The prior art cell culture methods employ submerged cell culture methods which use air flow agitation tank and so on. In the submerged cell culture methods, liquid medium is periodically or continuously supplied and taken out to cause continuous culture. However, these operations for culture have problems such as flow of proliferated cells, necessity of large culture apparatus, and necessity of large agitation power, so that it is difficult to continuously produce metabolites. Furthermore, when metabolites are not secreted into culture bath, it is very difficult to continuously and selectively take out cells in which much amount of metabolite is accumulated, so that batch operation is often used in this case.

The above proposed method and apparatus are different from the prior arts in that cells to be proliferated are attached to porous materials such as formed synthetic high polymer, namely, urethane foam, natural sponge, natural fiber such as cotton, or a porous material made of synthetic fiber and culture of cells is carried out in extremely high efficiency and furthermore liquid medium including metabolite is easily separated from cells. However, even in the above proposed apparatus cell culture can not be carried out continuously.

An object of this invention is to provide cell culture apparatus which make the most of properties of the above proposed method and make possible to produce metabolite continuously.

SUMMARY OF THE INVENTION

The above described problem is solved by this cell culture apparatus comprising a fluidized bed culture body in which cell attached porous material is fluidized by air flow and cells are proliferated, and a pre-culture tank for supplying medium to said fluidized bed culture body according to the amount of liquid medium which is taken out of said fluidized bed culture body.

This invention is different from the prior art cell cultures, specially the submerged culture in which cells are proliferated in batch-wise or continuous operation using a air flow agitator. In this invention, liquid medium including metabolite is taken out singly or along with some pieces of cell attached porous material and newly adjusted medium is supplied singly or along with porous material to the culture tank body so that metabolite is continuously produced.

More specifically, in this invention, liquid medium and porous material are firstly supplied to the air flow fluidized bed culture tank body. Diameter of the porous material is preferably below one tenth of a typical diameter of the fluidized bed culture tank body or below 10 mm and volume of the porous material is preferably 0.1 to 0.7 liter per one liter of liquid medium. After sterilization of the culture body, cells are inoculated into the culture body and air flow fluidized culture is started proliferation of cells is enhanced by biological film formed on surface of the porous material. By detecting the time when concentration of metabolite in the liquid medium reaches to a predetermined concentration or the time when concentration of substrate decreases to a predetermined concentration or by detecting cell growth state, the amount of produced metabolite or decrease of substrate through measurement of pH, DO, etc. in the liquid medium, the amount of liquid medium to be taken out and the time when takeout operation starts are determined. And then the liquid medium is taken out, being separated from cell attached porous material or along with some pieces of the cell attached-porous material from a drain pipe through a valve.

Through a supply pipe connected with the pre-culture tank through a valve, newly adjusted medium is supplied singly or along with the porous material to the fluidized bed culture tank, and air flow fluidization is continuously or sequentially carried out. As a result, cells attaching to porous material which remains in the fluidized bed culture tank makes possible to produce metabolite continuously.

A perforated valve having perforations smaller than the size of the porous material may be provided within the drain pipe so that the liquid material is separated from the cell attached porous material.

According to this invention, we can obtain the following advantages;

1. It becomes easy to carry out the takeout and supply operation on a condition adequate for growth properties of each kind of cells. Specifically, It becomes possible to carry out a continuous or sequential cell culture which has been difficult in the prior arts using a air flow agitator and recover objective metabolite separately and continuously. Therefore, this invention gives a very large effect on industrial production of metabolite.

2. Since this invention continuously or sequentially causes culture utilizing cells which have been attached to the porous material, it becomes possible to delete or shorten sterilization operation, cell inoculation operation and so on which are to be carried out for each batch process in the prior art batch wise culture methods. Production efficiency increases as a whole. In other words, productivity of a useful substance such as antibiotics( streptpmycin, cephamycin, oxytetracycline, erthoromycin, kanamycin, etc.), enzyme( amylase, protease, pectinase, cellulase, lipase, glucoamylase, glucoisomerase, etc.), protein( single cell protein, etc.), polysaccharide( arabinose, mannose, rhamnose, dextran, etc.), physiological active substance( vitamin $B_{12}$, vitamin$_2$, vitamin C, etc.), or animal or plant hormone auxin, cytokinin, gibberellin, steroid hormone, insulin, lymphokine, etc.) is enhanced. In sum, this invention can be refered to as a separator type bioreactor by which mass production can be continuously carried out and objective product can be recovered separately.

Hereinbelow, these and other effects will be described in detail by way of examples.

EXAMPLE

Figure 1:
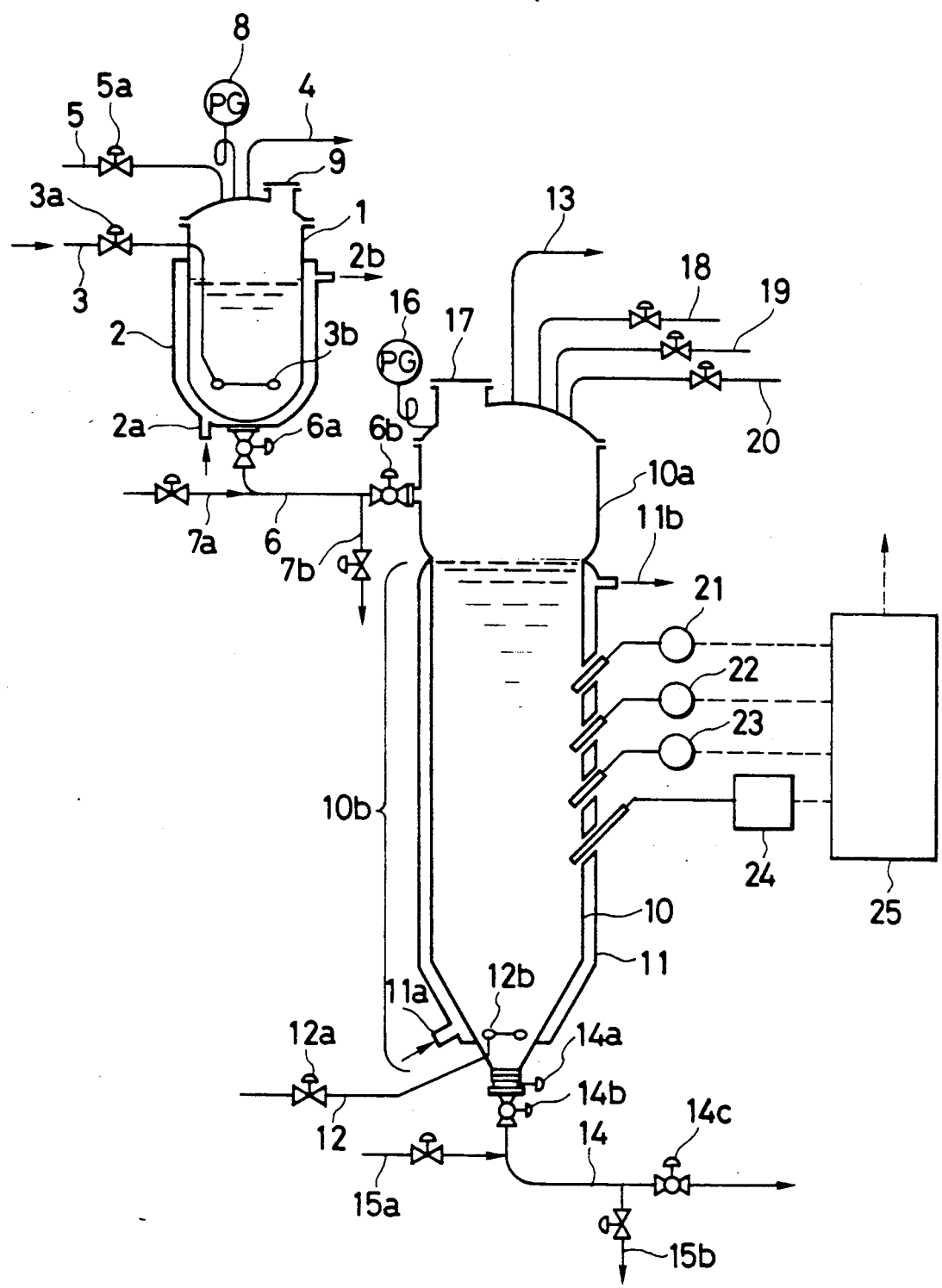
FIG. 1 is a schematic diagram of a prefered embodiment of this cell culture apparatus.

FIG. 1 shows a prefered cell culture apparatus according to this invention.

A cell culture apparatus according to this invention comprises a pre-culture tank 1 for supplying liquid medium and porous material or liquid medium only and a fluidized bed culture tank body 10. A supply pipe 6 having automatic control valves 6a, 6b connects the pre-culture tank 1 and the fluidized bed cell culture tank body 10 and transfers medium or porous material. A drain pipe 14 having automatic control valves 14a, 14b is provided at the bottom of the culture tank body 10 and drains liquid medium or porous material.

The automatic control valve 14a is provided toward the fluidized bed culture tank body 10 with respect to the automatic control valve 14b and has perforations smaller than the size of the porous material.

Supply pipes 7a, 15a for supplying sterilized and pressured air or vapor for sterilization and drain pipes 7b, 15b for draining liquid medium or porous material are also provided.

The upper part of the fluidized bed culture tank body 10 forms a freeboard, and the lower part forms porous material fluidized bed culture portion 10b.

Air flow pipes 3, 12 with automatic control valve 3a or 12a, air diffusers 3b, 12b, exhaust pipes 4, 13, porous material introduced ports 9, 17 are provided with the preculture tank 1 and the culture tank body 10, respectively. Constant temperature jackets 2, 11 are further provided around the tank 1 and tank body 11, respectively and temperature controlled water flows through the jackets 2, 11 from temperature controlled lower inlets 2a, 11a to temperature controlled upper outlets 2b, 11b so that culture is carried out under a predetermined culture temperature.

An inoculation nozzle 18, an acid/alkali injection nozzle 19, and anti-foaming agent injection nozzle 20 are provided with the culture tank body 10. A medium injection pipe 5 having an automatic injection valve 5a is provided with the pre-culture tank 1.

At the beginning of culture, porous material and medium of a predetermined amount for starting culture are taken into the fluidized bed culture tank body 10. After sterilization of those, cells are inoculated from the inoculation nozzle 18. Air, which may be enriched with oxygen, is introduced in a predetermined rate through the air flow pipe 12 and the air-diffuser 12b which is disposed at the bottom of the culture tank body 10 and has many openings smaller than the size of porous material. And then fluidized cell culture starts.

The culture condition is detected by a pH sensor 21, a DO sensor ( Dissolved Oxygen concentration meter 22, a temperature sensor 23, and an automatic analyzer 24 ( which causes regular sampling by means of a timer controller, and then automatically measures substrate and metabolite concentration by using a liquid chromatography and also may measure cell concentration by using a turbidity meter ). The detected values are monitored and recorded by a control device 25 including a computer. The control device compares a preprogramed changing pattern of concentration of metabolite or substrate or a preprogramed changing pattern of pH or DO value as indirect observations under culture with the detected values in order to estimate the time when the concentration of the metabolite in the liquid medium reaches to a predetermined concentration or the time when the concentration of the substrate reaches to a predetermined concentration. If a controller without a computer, e.g. a sequence controller is used, the time when the concentration reaches to a predetermined value is directly detected. As a result of the estimation, the time to start taking out and supplying liquid medium and porous material is determined. The amount of proliferated cells may be estimated from the amount of the produced metabolite and the amount of consumed substrate, further the amount of the cell attached porous material and liquid medium to be taken out is determined.

By actuating the automatic control valves, the porous material and the liquid medium of the determined amount are taken out through the drain pipe 14 disposed at the bottom of the fluidized bed culture tank body 10. New porous material and newly adjusted medium are supplied through the supply pipe 6 to the fluidized bed culture tank body 10 to carry out the fluidized culture continuously. If the sequencer controller is used, the time to change the porous material and the liquid medium is predetermined by a timer controller or determined by an indicated value of a level indicator, so that control for supplying porous material and liquid medium of the predetermined are carried out.

The above described operations may vary with kinds of cells, but in every cases, some pieces of cell attached porous material are left in the culture tank body 10.

The cells, which live in surface layer of the porous material left in the tank body 10, grow using the supplied new porous material and newly adjusted medium. Therefore, sterilization operation, inoculation operation and cell proliferation time, which have to be carried out for each batch process employed in submerged culture methods using a air flow agitator, can be deleted or shorted.

By repeatedly carrying out the culture operations as described, we can continuously cause cell growth by use of one fluidized bed culture tank. This embodiment is especially suitable for the case that an objective metabolite is produced by the secondary metabolism process as in molds. In this embodiment, objective product is continuously produced, that is the difference from the prior art batch wise culture methods.

Figure 2:
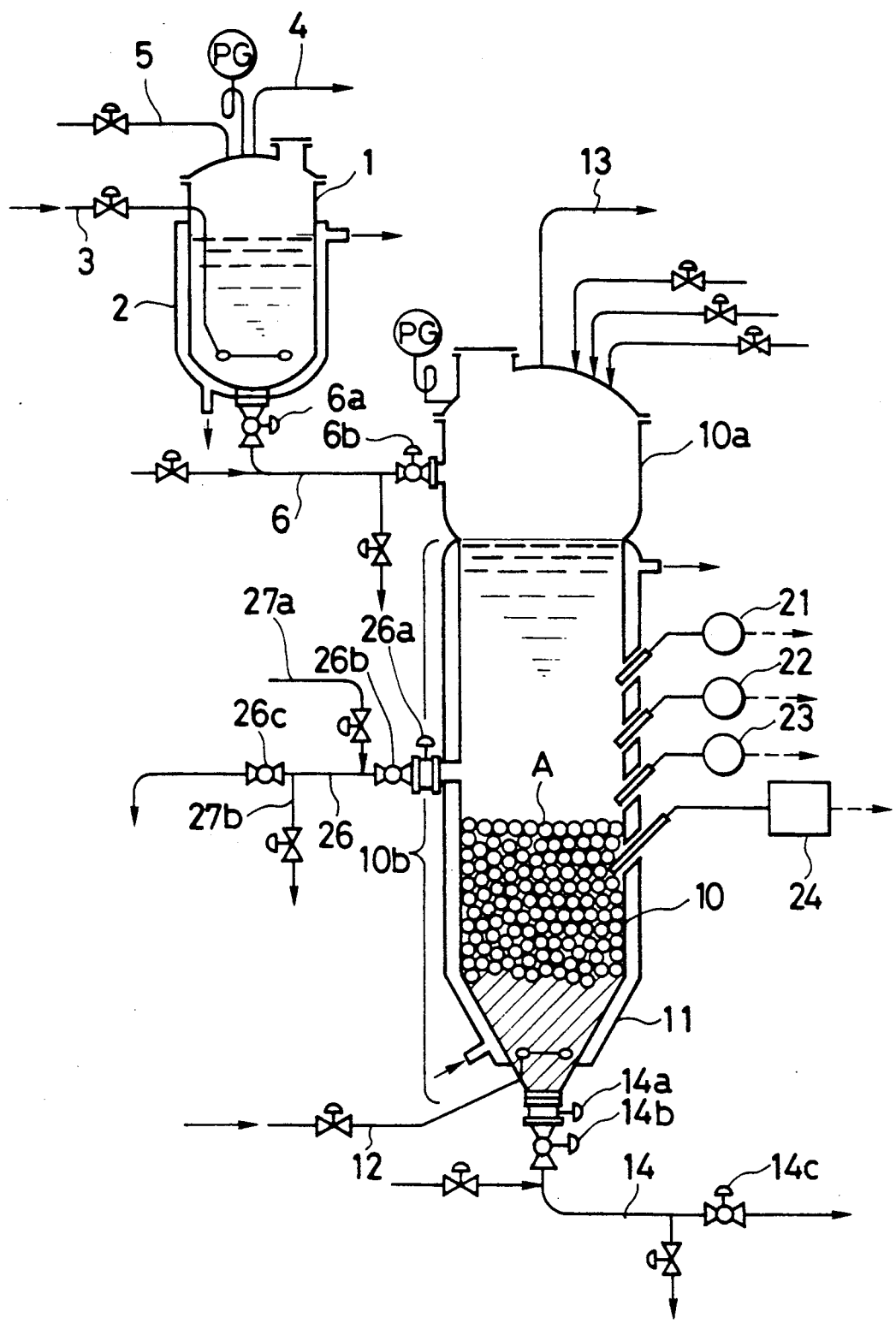
FIG. 2 is a schematic diagram of another prefered embodiment of this invention, which is used especially when liquid medium have to be separated from porous material.

FIG. 2 shows another prefered embodiment of this invention, which is used especially when liquid medium have to be separated from porous material and taken out.

A drawn pipe 26 with an automatic control porous valve 26a and automatic control drawn valves 26b and 26c are provided at the side of porous material fluidized culture portion 10a of the culture tank body 10 above a static porous material layer A which is formed in the porous material fluidized culture portion 10b while air flow stops. In this embodiment, the liquid medium can drains without friction of porous material and faster than the case that only liquid medium drains from the drain pipe 14, which is disposed at bottom of the culture tank body 10, through the automatic control valve.

Figure 3:
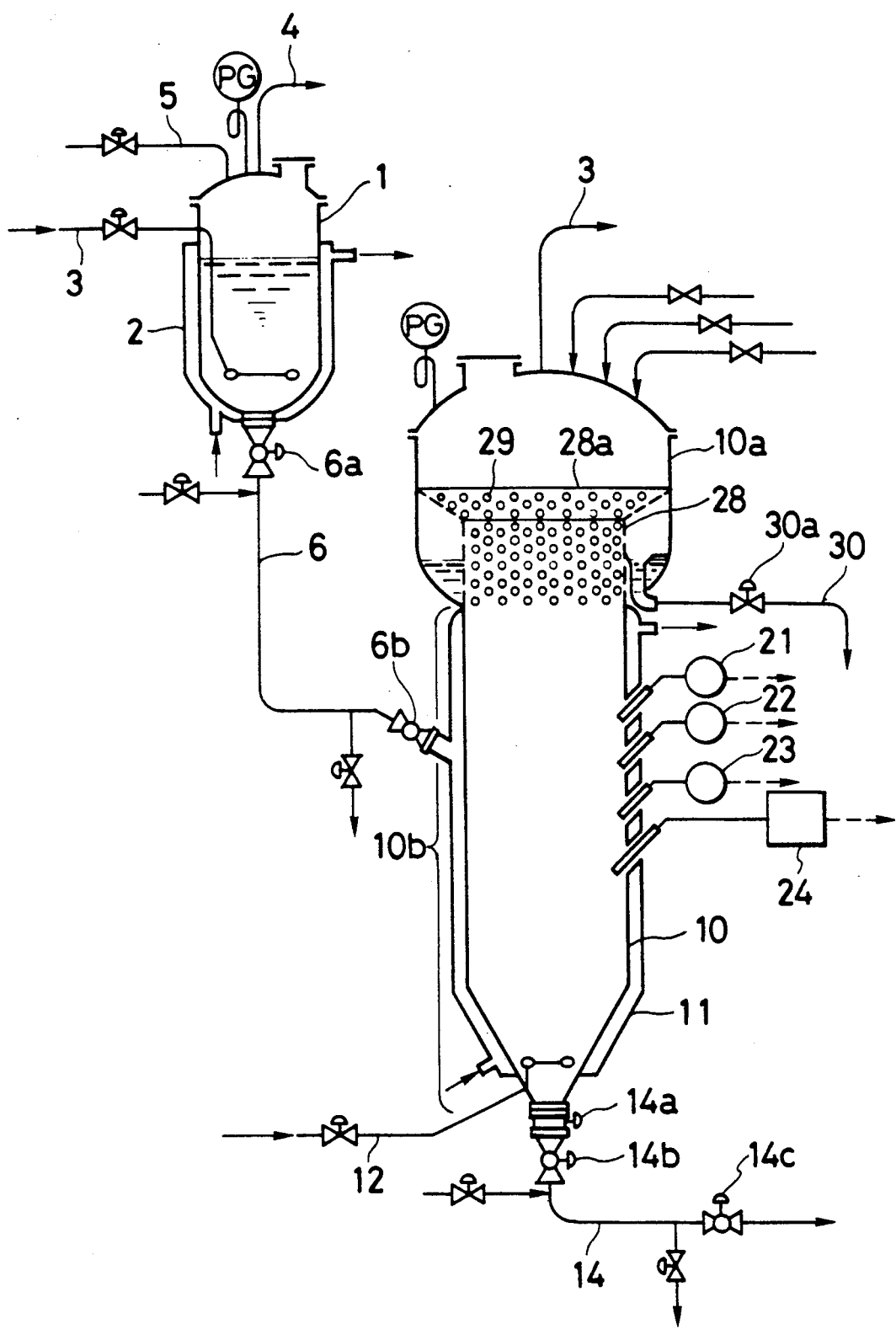
FIG. 3 is a schematic diagram of still another prefered embodiment of this invention, which is used when liquid medium is continuously taken out and supplied.

FIG. 3 shows still another prefered embodiment of this invention in which takeout operation and supply operation of liquid medium are continuously carried out.

A perforated cylinder 28 having many perforations 28a smaller than the size of porous material is provided within the upper freeboard 10a of the fluidized bed culture tank body 10 and connects to the porous material fluidized culture portion 10b. A perforated conical cylinder 29 connects to the top of the perforated cylinder 28 and contacts with the inner side of the freeboard 10a. A drain pipe 30 with an automatic control valve 30a is connected with the lower portion of the freeboard 10a. The supply pipe 6 from the bottom of the preculture tank 1 connects to the side of the porous material fluidized culture portion 10b below the parforated cylinder 28. The liquid medium of the same amount as that is continuously supplied from the pre-culture tank 1 is separated from the porous material by the parforations 28a of the perforated cylinder 28 and the parforated conical cylinder 29 and drains through the drain pipe 30.

The cell culture apparatus as constructed above is effective especially when much amount of cells should be proliferated or extracellular metabolite should be continuously separated and recovered.

Figure 4:
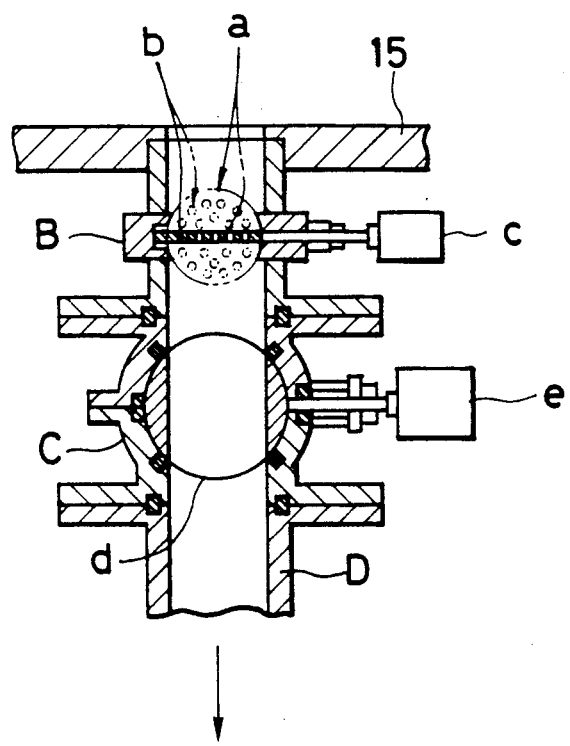
FIG. 4 is a sectional view of a valve which can passes only liquid medium through a drain or drawn pipe.

FIG. 4 shows a sectional view of a drain or drawn pipe which may be used in this invention.

An automatic control parforated valve body B, in which a parforated valve a having many parforations b is installed, is provided within the drain or drawn pipe D toward the culture tank body 15. An automatic control ball valve body C, in which a ball valve d is installed, is also provided within the drain or drawn pipe D on the downstream side with respect to the automatic control parforated valve body B When only culture liquid is drained from the culture tank body 15, the parforated valve a is rotated by a valve drive motor c to bea closed, and the ball valve d is rotated by a valve drive motor e to be opened. As a result of this, pieces of the porous material are intercepted by the parforated valve a and only liquid medium drains When the porous material and liquid medium are both drained, the parforated valve a is also opened and the porous material is drained along with the liquid medium It is needless to say that the automatic parforated valve body B and/or the automatic control ball valve C may be a butterfly valve or a flush valve, and further a pressurized air driven piston may be used instead of the valve drive motor.

Hereinbelow, experimental results using a cell culture apparatus according to this invention will be shown.

EXAMPLE 1

An example in which only liquid medium is changed

Pieces of cubic porous material about 5 mm in side length of urethane foam 160 g in total weight ( about 3000 cm$^3$ and 8 liter of liquid medium consisting of 40 g lactose, 20 g corn steep liquor, 3 g NaNO$_3$, 0.5 g KH$_2$PO$_4$, 0.25 g MgSO$_4$.7H$_2$O with one liter distilled water were put into a fluidized bed type culture tank of glass cylinder 17 cm in diameter. Next, the culture tank including the porous material and the liquid medium was sterilized. After this sterilization, Penicillium chrysogenum JCM2056 ( Q176) as penicillin production strain was inoculated. Culture temperature was kept at 24° C. by flowing temperature controlled water through the jacket. Air flow fluidized culture was started by flowing air at the rate of 30 l/min. pH of the liquid medium at the beginning of the culture was 4. The value of pH was monitored by the pH sensor and controlled so as not to exceed 6.

When the concentration of the produced penicilin became the maximum, that is, after 140 hours from the beginning of culture, 6 liter of the liquid medium was singly drawn out of the fluidized bed culture tank. 6 liter of the above medium with distilled water was supplied from the pre-culture tank to the fluidized bed culture tank. The initial concentration of lactose after this change of liquid medium was 25 g/liter. Then the air flow fluidized culture was carried out again. When 100 hours further lapsed, only the liquid medium was drawn and supplied, in a similar way as the first operation, so that the initial concentration of lactose after this change became 15 g/liter. Then, the air flow fluidized culture was restarted. When 90 hours furthermore lapsed, only the liquid medium was drawn and supplied again so that the initial concentration of lactose after this change became 10 g/liter, and then the air flow fluidized culture was restarted again. The results of this experiment are shown in FIG. 5.

Figure 5:
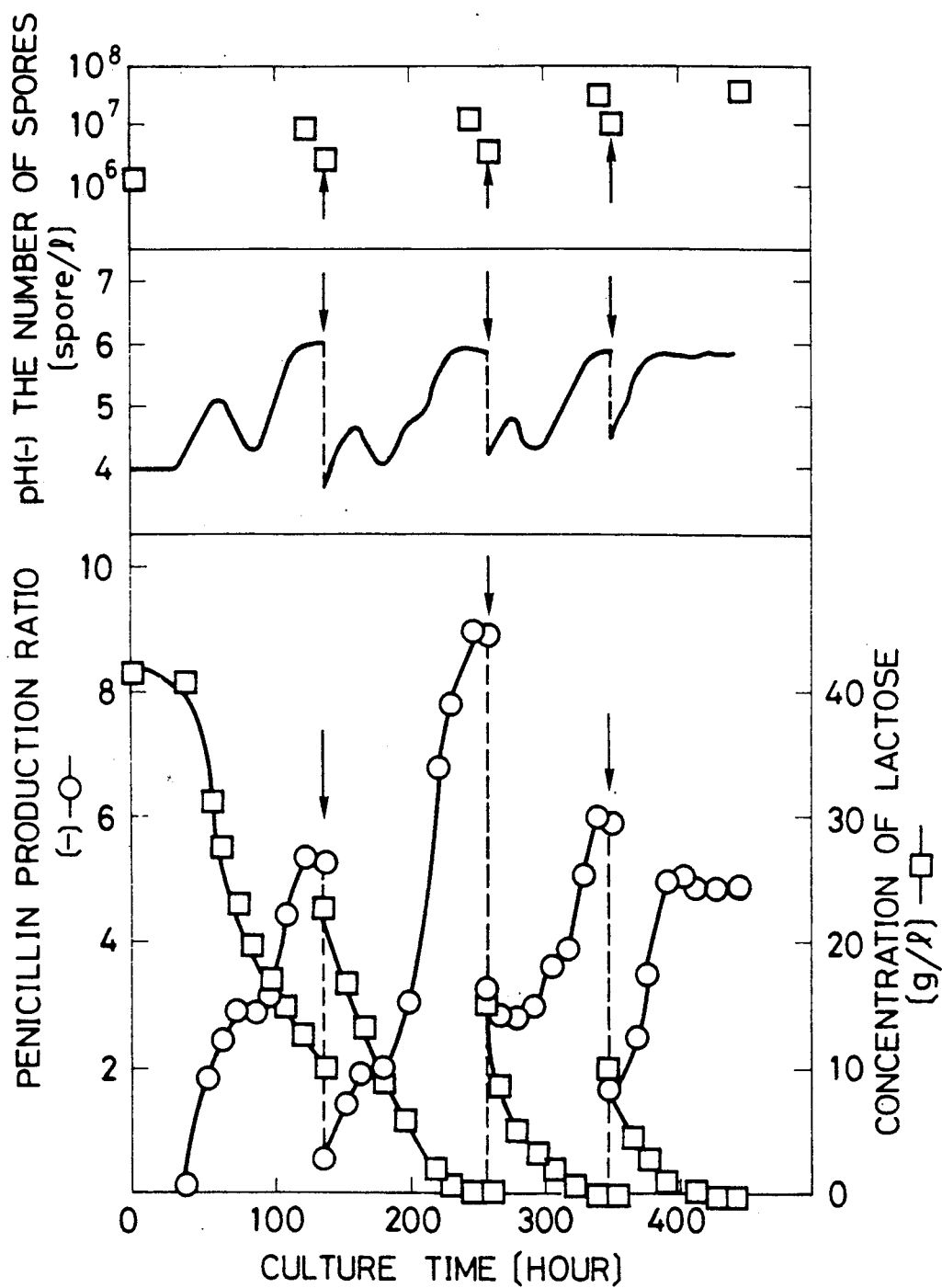
FIG. 5 is a graph showing time dependent properties of Penicillium chrysogenum JCM 2056 strain under the culture condition that only liquid medium is taken out and newly adjusted medium is supplied.

In FIG. 5, the amount of produced penicillin is shown in relative value, that is, penicillin production ratio (−) where unity is selected to the maximum amount of produced penicillin obtained on the seventh day from the beginning of the culture on the condition that 100 ml of the above liquid medium without urethane foam was put into a conical flask 300 ml in volume and culture was carried out by shaking culture at 200 rpm shaking rotational speed at 24° C. In FIG. 5, time dependent proparties of pH value and the number of spores are also shown.

After the changes of liquid medium, in each cases, ability to produce penicillin was maintained and penicillin tended to be produced in proportion to the initial concentration of lactose after the changes of medium. In the initial culture process just after the inoculation of cells, there was time duration while penicillin was not produced, however, production of penicillin was quickly restarted just after the exchanges of liquid medium.

During culture, concentration of penicillin increased in proportion to pH value, and tend to reach to the maximum concentration at 10 to 20 hours after pH reached 6. From the experimental results, it is found that pH indirectly showed the concentration of metabolite such as penicillin and may be used as an index for detecting the time to start drawing and supplying medium.

In this experiment, since the porous material was not changed, the amount of cells which grew in the surface layer of the porous material gradually increased, the number of spores in the liquid medium also increased and mycelium grew in the liquid medium. As a result, the liquid medium became turbid.

EXAMPLE 2

An example in which liquid medium and porous material are both changed.

Figure 6:
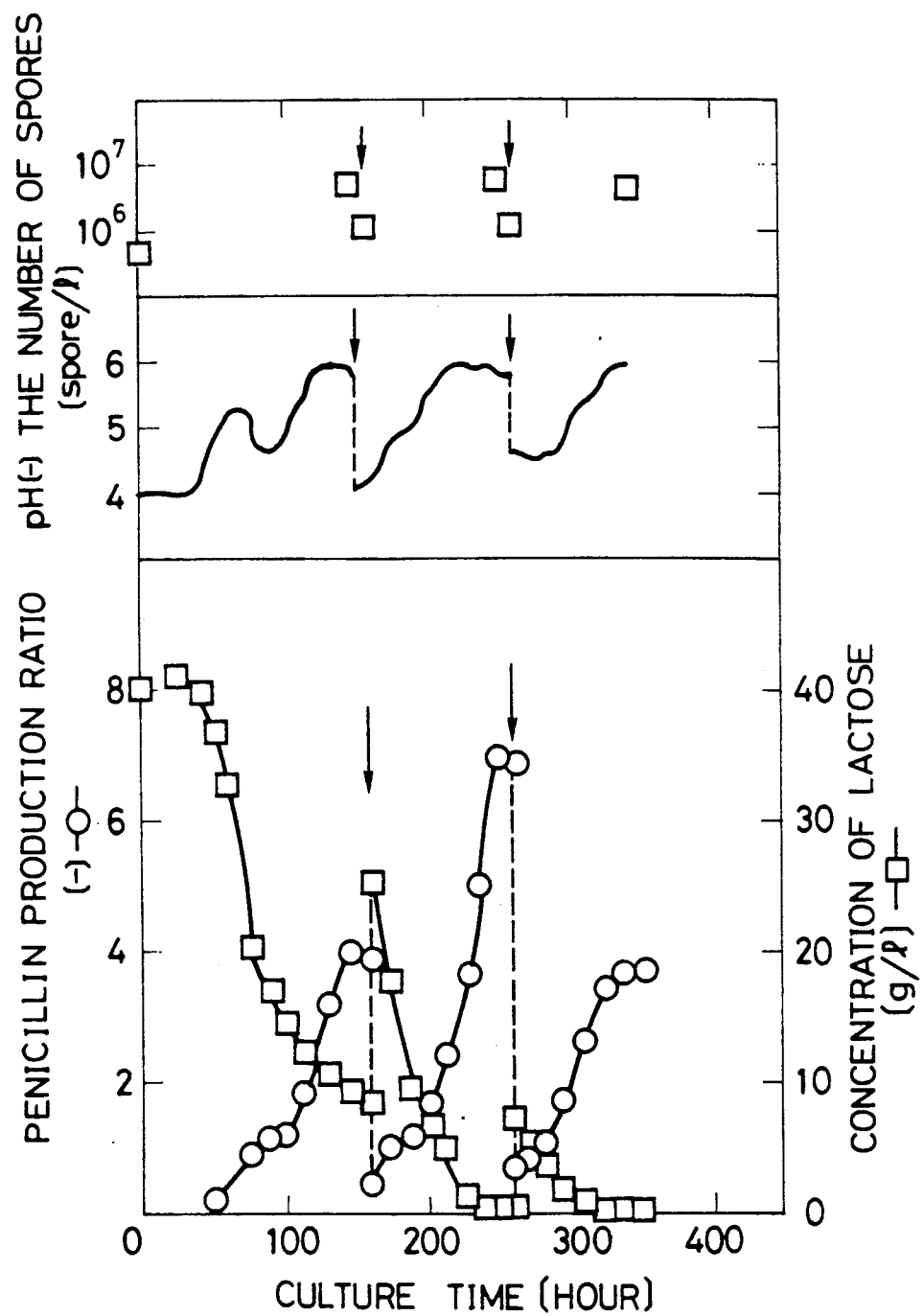
FIG. 6 is a graph showing time dependent properties of JCM 2056 strain under the culture condition that liquid medium and porous material are taken out, and newly adjusted medium and new porous material are supplied.

The same initial culture condition as EXAMPLE 1 was set. After 150 hours from the beginning of culture, 6.2 liter of the liquid medium and 30% of the porous material to the initially supplied amount were taken out and new porous material and the newly adjusted medium of the same amount for each as that was taken out were supplied, so that the initial concentration of lactose was 25 g/liter just after this change. Then air flow fluidized culture was started again. When 100 hours lapsed, in a similar manner as the first operation, 6.5 liter of the liquid medium and 50% of the porous material to the initially supplied amount was changed so that the initial concentration of lactose just after this change was 7.5 g/liter. The air flow culture was restarted. The results of this experiment are shown in FIG. 6.

Ability to produce penicillin was maintained after the changes of liquid medium and porous material as in EXAMPLE 1, and concentration of penicillin increased just after the changes.

When a part of pieces of mycelium attached porous material was taken out, and new porous material was supplied, it was found that mycelium grew on surface layer of the porous material, as a result, the number of spores in the liquid medium was kept constant, and growth of mycelium in the liquid medium was weaker than EXAMPLE 1.

As described above, by utilizing mycelium which is in initial culture process, culture can be carried out continuously in one culture tank. It is also found when objective metabolite to be produced is secondary metabolite which is produced in a period while growth of mycelium degenerates or on a low substrate concentration, objective metabolite can be continuously produced effectively by use of low initial substrate concentration which means decrease of sugar source to be consumed.

As this invention may be embodied in several forms without departing from the spirit of essential characteristics thereof, the above embodiments are therefore illustrative and not restrictive, since the scope of the invention is defined by the appended claims rather than by the description proceeding them, and all changes that fall within meets and bounds of the claims, or equivalence of such meets and bounds are therefore intended to be embraced by the claims.

What is claimed is:

1. A cell culture apparatus for proliferation of cells on porous material in a liquid medium by repetitive batch operation comprising:
    (a) a fluidized bed culture tank, in which cells attached to porous material are fluidized by air flow;
    (b) a pre-culture tank for supplying liquid medium to said fluidized bed culture tank;
    (c) a supply pipe connecting said pre-culture tank to said fluidized bed culture tank through which liquid medium is supplied;
    (d) a drain pipe connected to the bottom of said fluidized bed culture tank; and
    (e) drain valve means for controlling flow through said drain pipe, wherein said drain valve means comprises first valve means constructed and arranged so as to prevent flow through said drain pipe when in a first position and to permit flow through said drain pipe when in a second position and second valve means constructed and arranged so as to cooperate with said first valve means and to permit flow of both liquid growth medium and porous material through said drain pipe when in a first position and to permit flow of liquid growth medium but not porous material through said drain pipe when in a second position.

2. A cell culture apparatus according to claim 1, further comprising supply valve means for controlling flow of liquid medium through the supply pipe.

3. A cell culture apparatus according to claim 1, further comprising an outlet pipe connected to a side portion of said fluidized bed culture tank and outlet valve means for controlling flow through said outlet pipe, wherein said outlet valve means comprises first valve means constructed and arranged so as to prevent flow through said outlet pipe when in a first position and to permit flow through said outlet pipe when in a second position and second valve means constructed and arranged so as to cooperate with said first valve means of said outlet valve means and to permit flow of both liquid growth medium and porous material through said outlet pipe when in a first position and to permit flow of liquid growth medium but not porous material through said outlet pipe when in a second position.

4. A cell culture apparatus in accordance with claim 1, wherein said second valve means comprises a perforated valve body having openings sized to prevent the passage of porous material past the perforated valve body.

5. A cell culture apparatus according to claim 4, wherein the first valve means comprises a solid valve body and wherein the perforated valve body is disposed between the solid valve body and the fluidized bed culture tank.

6. A cell culture apparatus according to claim 1, further comprising monitoring means for monitoring and providing a signal indicative of the progress of cell growth within the fluidized bed culture tank.

7. A cell culture apparatus according to claim 6, further comprising control means for controlling said drain valve means in response to the signal from said monitoring means.

8. A cell culture apparatus according to claim 1, further comprising means for continuously removing liquid medium from the fluidized bed culture tank.

9. A cell culture apparatus according to claim 8, wherein said culture tank includes an upper section, and wherein said continuous removal means comprises perforated separator means disposed within said upper section of the culture tank so as to define a separate drainage space and a liquid removal pipe connected to the culture tank and in communication with said drainage space.

10. A cell culture apparatus according to claim 9, wherein said culture tank further includes a cylindrical lower portion with an upper end and a cylindrical upper portion of greater diameter than said lower portion, and wherein said perforated separator means comprises a cylindrical lower portion with an upper end of the same diameter as said cylindrical lower portion of the tank and extending from the upper end of said cylindrical lower portion of the tank into said cylindrical upper portion of the tank and a conical upper portion which extends from the upper end of said cylindrical lower portion of the separator means to the side walls of the cylindrical upper portion of the tank.

* * * * *